United States Patent [19]

Kley

[11] Patent Number: 4,604,648
[45] Date of Patent: Aug. 5, 1986

[54] ELECTRONIC VIEWING SYSTEM FOR INTEGRATED CIRCUIT PACKAGES

[76] Inventor: Victor B. Kley, 1119 Park Hill Rd., Berkeley, Calif. 94708

[21] Appl. No.: 660,275

[22] Filed: Oct. 12, 1984

[51] Int. Cl.[4] ............................................. H04N 7/18
[52] U.S. Cl. ...................... 358/101; 358/93; 362/89; 362/227; 362/249; 362/250; 362/251; 362/252
[58] Field of Search .................. 358/101, 106, 107, 93, 358/95; 250/571, 572; 356/237; 362/85, 89, 227, 249, 250, 251, 252

[56] References Cited

U.S. PATENT DOCUMENTS

| | | | |
|---|---|---|---|
| 3,903,363 | 9/1975 | Montone | 358/101 |
| 4,025,777 | 5/1977 | Hayakawa | 362/250 |
| 4,028,728 | 6/1977 | Sharp | 358/106 |
| 4,072,928 | 2/1978 | Wilder | 358/101 |
| 4,095,464 | 6/1978 | Breedijk | 358/101 |
| 4,556,903 | 12/1985 | Butchington | 358/101 |

*Primary Examiner*—Howard W. Britton
*Attorney, Agent, or Firm*—Bernard, Rothwell & Brown

[57] ABSTRACT

A system for viewing circuit leads mounted on glassy substrates employs unidirectional illumination at an acute angle selected to avoid impingement of direct reflected light onto the objective of the viewing system. Selecting the direction of the light to extend in a vertical plane parallel to parallel fingers or leads eliminates reflections from interdigital areas which have mirror-like concave surfaces due to menisci of the glassy surface at the metal lead edges.

7 Claims, 4 Drawing Figures

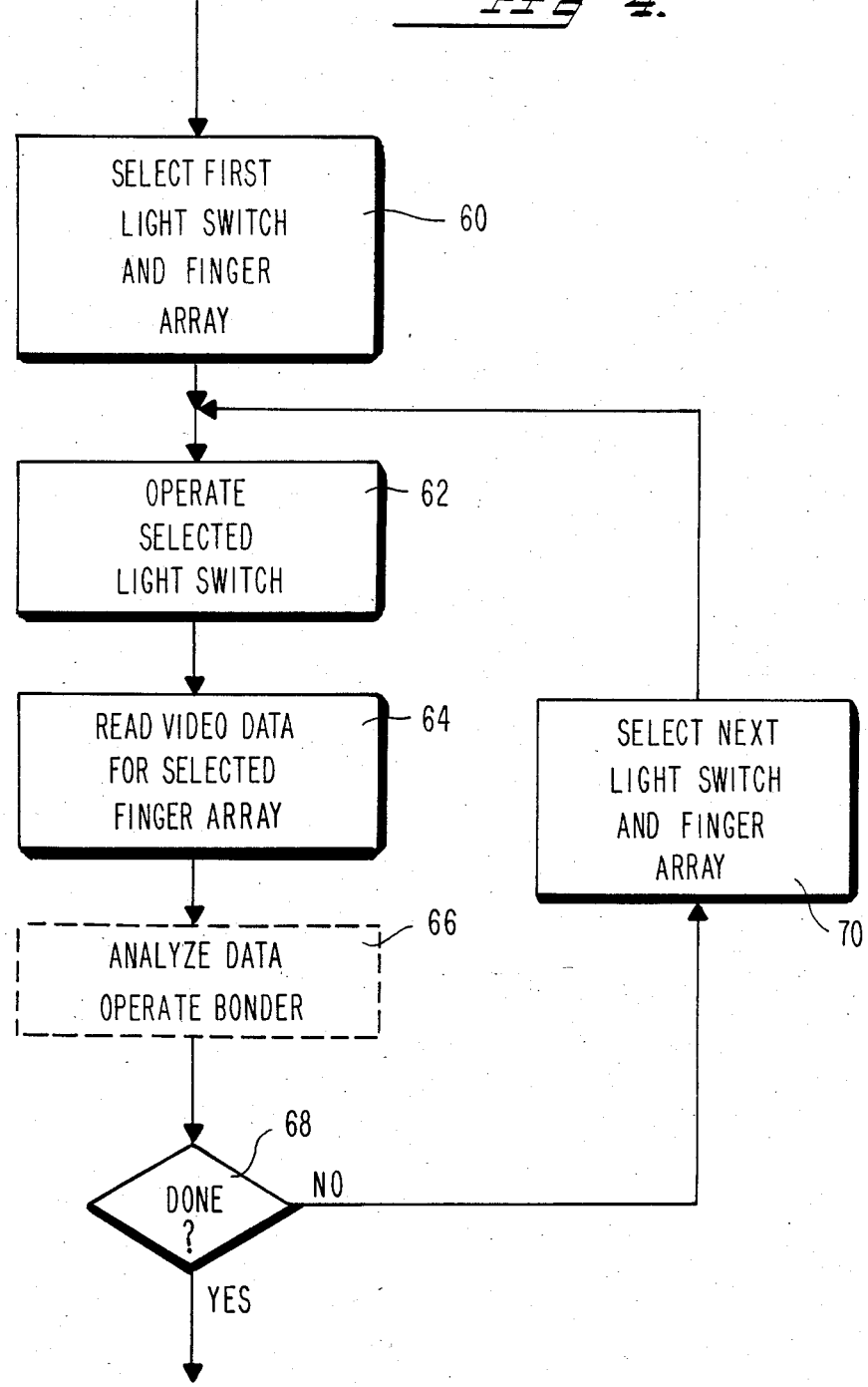

ELECTRONIC VIEWING SYSTEM FOR INTEGRATED CIRCUIT PACKAGES

TECHNICAL FIELD

The present invention relates to electronic viewing systems for generating electrical signals indicative of circuit patterns, particularly for use in automatic manufacturing procedures such as automatic wire bonding of integrated circuits to lead frames on glassy substrates.

DESCRIPTION OF THE PRIOR ART

Automatic integrated circuit manufacturing procedures, such as the automatic bonding of wire leads between integrated circuit chips and lead frames, include electronic viewing systems which produce electronic signals indicative of images of the integrated circuits and the leads or fingers in the lead frames. These electronic image signals are analyzed by computers to determine the exact positions of the fingers and integrated circuit portions for enabling the bonder to accurately bond wire leads to the respective fingers and integrated circuit portions. While these viewing systems work reliably for lead patterns and integrated circuits mounted on dull and contrasting substrates, the viewing systems do not operate reliably utilizing amorphic or glassy substrates. The shiny surfaces of such amorphic or glassy substrates reflect light which produces light spots and lines causing errors in analyzing of the video information to determine the exact location of fingers in the lead frame. Previous attempts, including improved digital analyzing techniques and/or different lighting techniques such as dark field illumination, have been unsuccessful in overcoming this problem.

SUMMARY OF THE INVENTION

The invention is summarized in an electronic viewing system wherein a finger pattern on an amorphic substrate is illuminated by substantially unidirectional incident light projected at an acute angle relative to the plane of the metal fingers such that directly reflected light from the fingers and amorphic substrate do not impinge upon the objective of a video camera imaging the finger pattern.

An objective of the invention is to provide a viewing system for metal fingers on an amorphic substrate wherein the effects of spectral reflections from the substrate are substantially eliminated.

An advantage of the invention is the recognition that amorphic or glassy surfaces produce substantially less scattered reflective light than metallic or crystalline surfaces so that illumination by unidirectional light in a direction selected to avoid direct reflections from the amorphic substrate impinging on the viewing objective eliminates false imaging of substrate regions by the viewing system.

One feature of the invention is the recognition that concave mirror-like surfaces formed by menisci of a glassy substrate surface between parallel horizontal groups of fingers are anamorphic or cylindrical, and light projected along vertical planes parallel to the fingers substantially avoids spectral reflections from the substrate regions reaching the viewing objective.

Another feature of the invention is the provision of selectable illumination at different angles of incidence to accommodate viewing systems with different numerical apertures or fields of view, or to accommodate systems with variable or plural changeable lens systems providing different selectable numerical apertures.

Other objects, advantages and features of the invention will be apparent from the following description of the preferred embodiment taken in conjunction with the accompanying drawings.

BRIEF DESCRIPTION OF THE DRAWINGS

FIG. 4 is a flow chart of a modification for a computer program for operating the illumination system of FIG. 1.

DESCRIPTION OF THE PREFERRED EMBODIMENT

Figure 1:
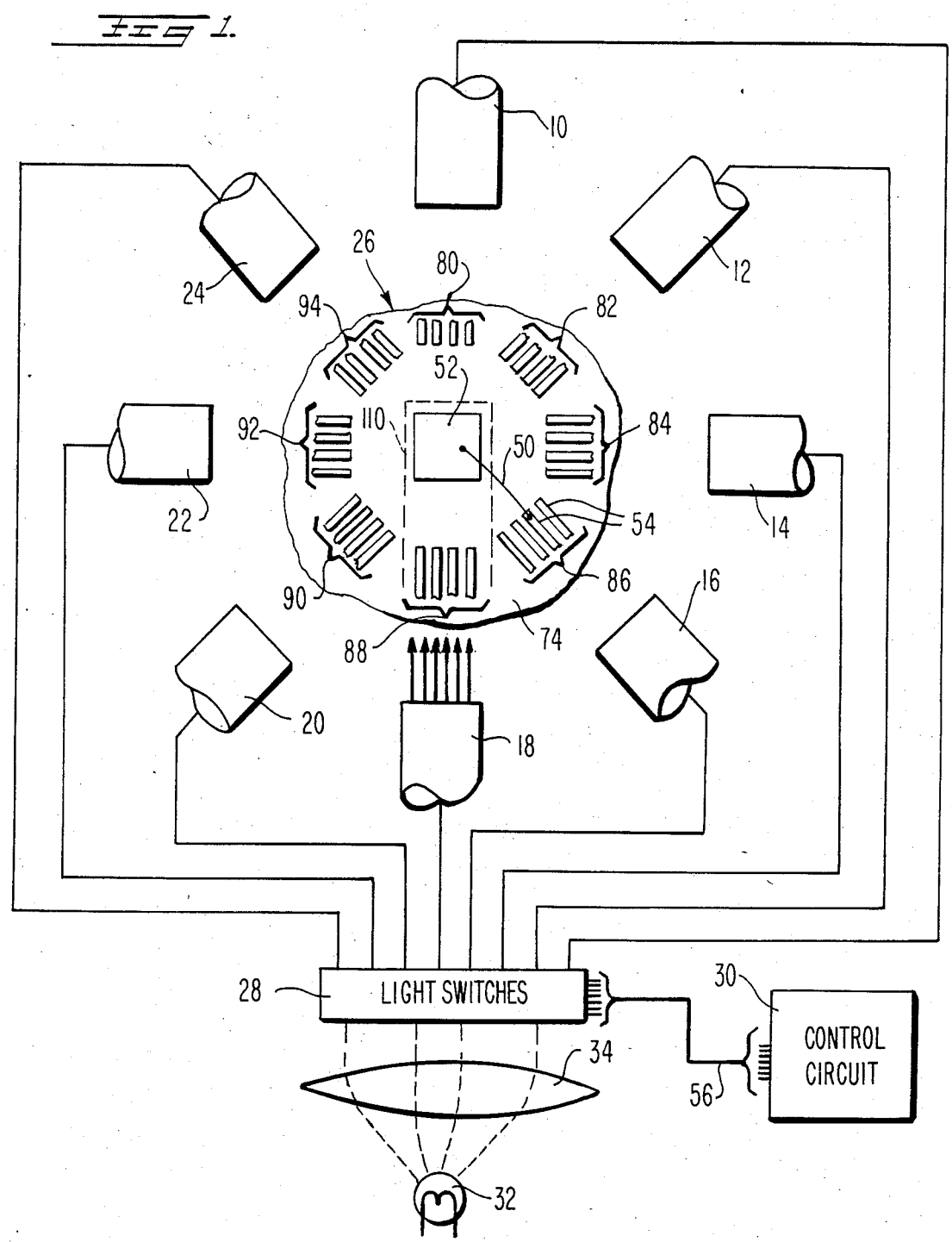
FIG. 1 is a diagram of an illumination system for use in an electronic viewing system for integrated circuit packages in accordance with the invention.
Figure 3:
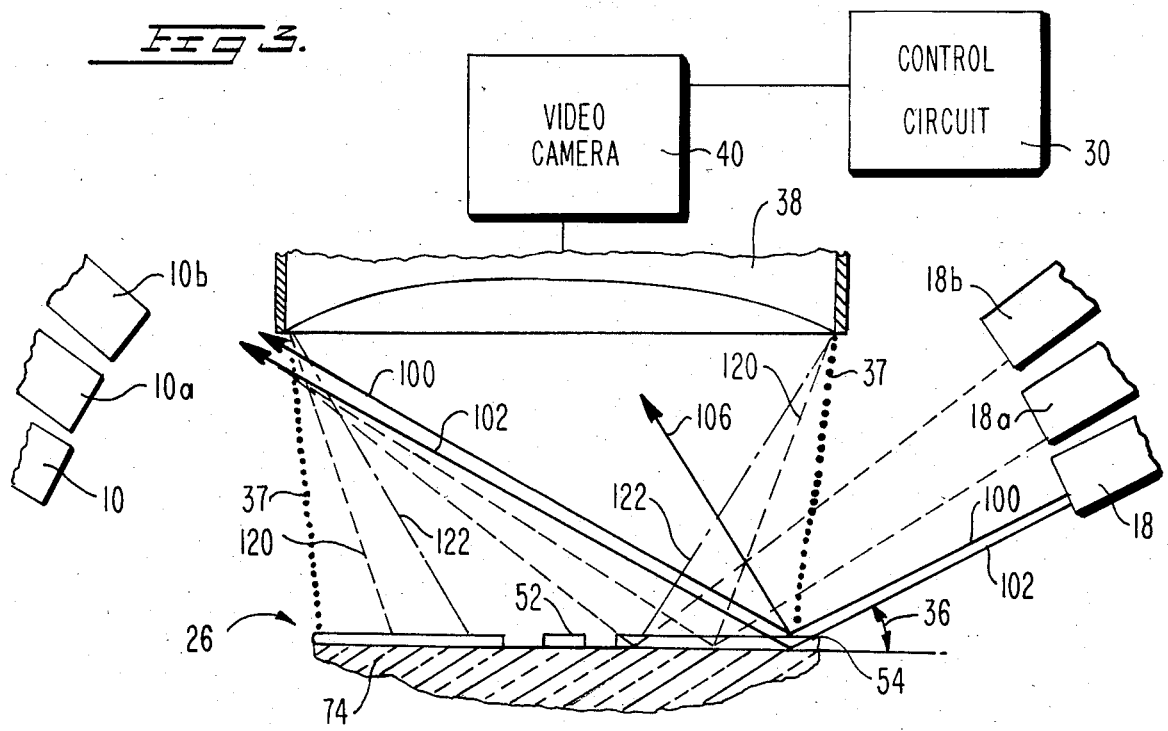
FIG. 3 is a diagram illustrating in elevation, the viewing system of the invention.

As illustrated in FIG. 1, one embodiment of the invention utilizes an illumination system having a plurality of electronic light sources, such as fiber-optic bundles 10, 12, 14, 16, 18, 20, 22 and 24, disposed in a circular array around a work station receiving an integrated circuit package, such as that shown generally at 26 enlarged relative to the size of the fiber-optic bundles. The fiber-optic bundles 10, 12, 14, 16, 18, 20, 22 and 24 are selectively energized with light from light switch unit 28 which, for example, is an electro-optic cell having a corresponding plurality of shutter patterns operated by electrical signals from a control circuit 30 for passing light from a suitable light source such as a tungsten halogen lamp 32 to the respective fiber-optic bundles. A condenser lens 34 is disposed between the lamp 32 and the light switch unit 28 for collimating the light applied to the unit 28. Alternatively, the unit 28 may be an array of electro-mechanical shutters controlling light entrance to the fiber-optic bundles, or the fiber-optic and light switch arrangement may be replaced by a circular array of individually operated light sources. As shown in FIG. 3, the light sources are disposed relative to the work station such that the light therefrom is directed obliquely onto the horizontal surfaces of the integrated circuit package 26 at an acute angle 36 selected such that directly reflected light from horizontal surfaces of the integrated circuit package 26 within the field of view, as shown by dotted line 37, does not impinge upon the objective 38 of an image detecting device such as a video camera 40, light sensing element array, etc., generating electrical image signals applied to the control circuit 30.

Figure 2:
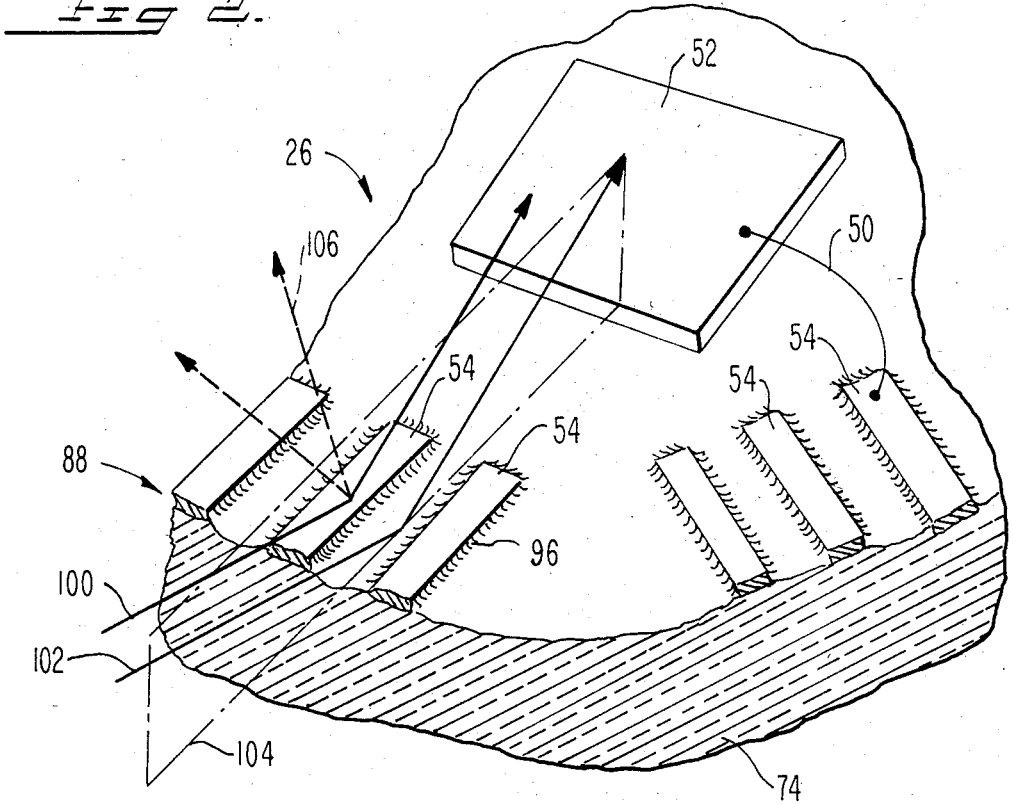
FIG. 2 is a perspective view of a broken-away portion of an integrated circuit package on which the invention is useful.

The described illumination system particularly enables the use of automatic wire bonders on integrated circuit packages 26 which have amorphic or glass substrates 74 upon which the integrated circuit chip 52 and metal leads with fingers 54 are mounted. In forming the package 26, a metal lead frame, having groups 80, 82, 84, 86, 88, 90, 92 and 94 of the fingers 54 arranged in a circular pattern wherein the fingers in each individual group are parallel and extend generally radially in the circular pattern, is mounted on the glass substrate 74 using a procedure wherein the upper glass surface forms concave menisci 96, FIG. 2, with the edges of the metal fingers 54. These menisci formed concave mirror-like surfaces which, in the prior art, produced reflections that cause errors in the analyzing procedures to distinguish between finger areas 54 and the interdigital areas between the fingers 54. The present invention overcomes this difficulty by sequentially directing oblique incident dark field light beams from corresponding directions wherein each direction corresponds to a selected group of fingers laying in a horizontal plane and defines a vertical plane extending parallel to the selected group of fingers. This is illustrated in FIG. 2 by the light rays 100 and 102 extending in a direction defining vertical plane 104 which is parallel to the longitudinal dimensions of fingers 54 in group 88 and is perpendicular to the horizontal plane defined by the group of fingers 88. The menisci reflector surfaces formed between the fingers 54 are found to be anamorphic, particularly to be cylindrical with reflective surfaces defined by parallel straight lines which are parallel to the longitudinal direction of the fingers 54. Light ray 102 incident to the interdigital area between fingers 54 being viewed is substantially completely reflected at an angle which, even when oblique to plane 104 due to reflection from a curved meniscus 96, will be in a direction avoiding impingement of the reflected ray on the objective 38 of the image detecting device 40. The metal fingers 54 are polycrystalline rather than being amorphic and thus produce a substantial scattered reflection such as shown by scattered ray 106, FIG. 2, impinging upon the objective 38. The difference between scattered radiation from finger surfaces 54 and the interdigital glassy surfaces is found sufficient to produce enough contrast in the imaging device 40 that the areas of the fingers 54 can be readily determined by the control circuit 30.

The automatic wire bonding apparatus automatically bonds wire leads 50 between selected points of an integrated circuit chip 52 and metal fingers 54 of the package 26. The conventional control circuit 30 which includes a microcomputer is modified to include additional computer controlled outputs 56 suitable for operating the light switching unit 28. Additionally, the program for the microcomputer in the circuit 30 is modified as shown in FIG. 4 to provide for sequentially operating the light sources 10, 12, 14, 16, 18, 20, 22 and 24 of FIG. 1. In step 60 the sequencing is set to select the first light switch and corresponding group of fingers so that in the following step 60 the selected first light switch is operated. Then in step 64 the video signal from the image detector 40 is sampled and stored to produce digital data which can be analyzed to determine the exact positions of the fingers 54 in the selected group in a conventional manner. The analyzing can be accomplished in optional step 66 during the sequential operation of the light sources or can be done later after the data corresponding to each of the finger groups has been sampled and stored. Also in step 66 the bonder can be operated to bond the wire leads between the fingers in the group of fingers just analyzed and the integrated circuit chip which in this case has been viewed and analyzed prior to step 60; this enables use of a smaller memory since only data concerning one group of fingers need be stored at one time compared to the memory required to store data concerning all of the groups of fingers. From step 66, or step 64 if step 66 is performed later, the program proceeds to step 68 where the program branches to step 70 if the bonding or storage of data has not been completed. In step 70 the next light switch and corresponding group of fingers are selected so that the program can proceed again to step 62 to repeat the light switch operating and data reading procedures for the newly selected light switch and group of fingers. When all the light sources have been operated and the corresponding data read and possibly analyzed, the program in step 68 proceeds to normal operating procedures.

The light sources 10, 12, 14, 16, 18, 20, 22 and 24 can illuminate the entire upper surface of the circuit package 26 with light directed in the corresponding directions, or the light may be patterned to illuminate only a selected area such as the area outlined by dashed line 110 or an even smaller area encompassing only the general area of the group of fingers being analyzed. The fiber-optic structure can be used to define the illumination pattern, or light pattern techniques such as those in my copending patent application Ser. No. 644,116, filed Aug. 24, 1984, and incorporated by reference herein, can be used. Additionally other illumination techniques such as wire bond integrity testing as described in the above incorporated copending application may be used in conjunction with the viewing system.

In a preferred embodiment as illustrated in FIG. 3, there is included one or more additional arrays of selectably energizable light sources, such as illustrated by an array including light sources 10a and 18a, and an array including light sources 10b and 18b, which provide for selective illumination at different angles of incidence relative to the horizontal plane of the circuit package 26, as well as in different radial directions defined by the light sources in each array. These additional light sources are selectively energized by corresponding additional light switches in the unit 28. This enables the illumination system to accommodate different viewing systems which have different magnifications or objective lens systems with different numerical apertures, or to accommodate viewing systems having interchangeable objective lenses with different numerical apertures or having variable or zoom objective lenses wherein the numerical aperture is selectively changed to change the field of view. Dashed lines 120 and long and short dashed lines 122 represent two possible different cones of acceptance for the objective 38 to define different fields of view on the circuit package 26 or to define different magnifications of the circuit portions being viewed. It is desirable for the incidence angle 36 to be as large as possible without producing direct reflections from the field of view onto the lens system; higher angles of incidence produce a higher intensity of scattered light from the metal circuit patterns 54 to enable better response of the light detector facilities in the imaging device 40. Thus, the light source arrays 10a, .. . 18a, . . . and 10b, . . . 18b, . . . are used when the objective 38 is set at or has a numerical aperture corresponding to the respective cones 120 and 122 to provide improved image detection. The light sources in the corresponding selected array are sequentially energized to sequentially illuminate the circuit package with light substantially collimated in directions defining vertical planes parallel to respective groups 80, 82, 84, 86, 88, 90, 92 and 94 of the fingers 54 in the same manner as described above for a single array.

The present illumination system is also believed to be suitable for integrated circuit package manufacturing procedures other than the described wire bonding application. For example, the illumination system can be utilized for integrated circuit package inspection systems, or may be used in manual operations wherein the video camera 40 is replaced by eye pieces and the illumination system is employed to substantially enhance the visibility of the corresponding lead and substrate regions of the package.

Since many modifications, variations and changes in detail may be made to the above described embodiment, it is intended that all matter shown in the foregoing description and in the accompanying drawings be interpreted as merely illustrative of the invention and not limiting to the scope and spirit of the invention as defined in the following claims.

It is claimed:

1. A system for viewing spaced metal fingers mounted in a plane on an amorphic substrate to generate electrical signals indicative of the finger pattern, comprising utilizing means for receiving light indicative of the finger pattern, an objective for being positioned over the finger pattern and for receiving and directing light from a field of view of the finger pattern to the utilization means, light source means for illuminating the finger pattern with generally unidirectional light, said light source means projecting the unidirectional light in a direction forming an acute angle relative to the plane of the metal fingers, and said acute angle and direction being selected so that directly reflected light from the fingers and amorphic substrate within the field of view avoids impingement upon the objective whereby scattered reflective light from the metal fingers impinges upon the objective to form an image of the metal fingers in the utilization means.

2. An electronic viewing system as claimed in claim 1 wherein the metal fingers are parallel, the amorphic substrate includes concave menisci formed along the edges of the fingers, and the angle of projected light defines a plane perpendicular to the finger plane and which is parallel with the metal fingers.

3. An electronic viewing system as claimed in claim 1 wherein the metal fingers include a plurality of groups of metal fingers with the fingers in each group being parallel to each other and the plurality of groups extending at different directions in the plane of fingers; and the light source means includes means for selectively projecting light onto the fingers from a plurality of different directions corresponding to the different directions of the finger groups but at acute angles relative to the plane of fingers such that the acute angles are each less than an angle at which directly reflected light from the fingers and amorphic substrate impinge upon the objective.

4. An electronic viewing system as claimed in claim 3 wherein the amorphic substrate includes concave menisci formed along the edges of the fingers, and the directions of light projection define respective vertical planes which are parallel to the corresponding groups of fingers.

5. An electronic viewing system as claimed in claim 3 wherein the means for selectively projecting light includes light switch means for being selectively operated to project unidirectional light sequentially from the respective plurality of directions.

6. An electronic viewing system as claimed in claim 5 wherein the amorphic substrate includes concave menisci formed along the edges of the fingers, and the directions of light projections define respective planes perpendicular to the finger plane and which are parallel with the corresponding groups of fingers.

7. An electronic viewing system as claimed in claim 3 wherein the light source means additionally includes means for selectively projecting light at different selected angles of incidence relative to the plane of fingers in correspondence with respective different numerical apertures of the objective.

* * * * *